United States Patent
Moshe et al.

(10) Patent No.: US 10,588,613 B2
(45) Date of Patent: Mar. 17, 2020

(54) CARDIAC TISSUE ANCHORING DEVICES, METHODS, AND SYSTEMS FOR TREATMENT OF CONGESTIVE HEART FAILURE AND OTHER CONDITIONS

(71) Applicant: BioVentrix, Inc., San Ramon, CA (US)

(72) Inventors: Meir Moshe, San Ramon, CA (US); Lon Annest, San Ramon, CA (US); Kevin Van Bladel, San Ramon, CA (US)

(73) Assignee: BioVentrix, Inc., San Ramon, CA (US)

( * ) Notice: Subject to any disclaimer, the term of this patent is extended or adjusted under 35 U.S.C. 154(b) by 680 days.

(21) Appl. No.: 14/471,973

(22) Filed: Aug. 28, 2014

(65) Prior Publication Data

US 2015/0066082 A1 Mar. 5, 2015

Related U.S. Application Data

(60) Provisional application No. 61/872,556, filed on Aug. 30, 2013.

(51) Int. Cl.
*A61B 17/04* (2006.01)
*A61B 17/00* (2006.01)
*A61B 17/30* (2006.01)

(52) U.S. Cl.
CPC ...... *A61B 17/0401* (2013.01); *A61B 2017/00243* (2013.01); *A61B 2017/00247* (2013.01);
(Continued)

(58) Field of Classification Search
CPC ........ A61B 17/0401; A61B 2017/0409; A61B 2017/0411; A61B 2017/00243–00256;
(Continued)

(56) References Cited

U.S. PATENT DOCUMENTS 3,737,579 A 6/1973 Bolduc
4,010,758 A 3/1977 Rockland et al.
(Continued)

FOREIGN PATENT DOCUMENTS

EP 1078644 A1 2/2001
WO 00/06028 A1 2/2000
(Continued)

OTHER PUBLICATIONS

International Search Report and Written Opinion of PCT Application No. PCT/US06/22594, dated Oct. 1, 2008, 4 pages.
(Continued)

*Primary Examiner* — Tan-Uyen T Ho
*Assistant Examiner* — Charles M Wei
(74) *Attorney, Agent, or Firm* — Kilpatrick Townsend & Stockton LLP

(57) ABSTRACT

A heart tissue gripping device may include a body portion, an elongate shaft, and a tissue gripping member that is attached to the distal end of the elongate shaft. The tissue gripping member being may be positioned adjacent a heart surface by insertion through an incision in the body. The tissue gripping member may releasably attach to tissue of the heart surface to facilitate a surgical instrument in performing one or more procedures. A coupling of the tissue gripping member may releasably attach the surgical device to the tissue gripping member to allow the device to access the tissue of the heart surface.

8 Claims, 11 Drawing Sheets

(52) U.S. Cl.
CPC ............... *A61B 2017/00358* (2013.01); *A61B 2017/00946* (2013.01); *A61B 2017/0404* (2013.01); *A61B 2017/0417* (2013.01); *A61B 2017/0464* (2013.01); *A61B 2017/0496* (2013.01); *A61B 2017/306* (2013.01)

(58) Field of Classification Search
CPC .. A61B 2017/00358; A61B 2017/0404; A61B 2017/0496; A61B 2017/306; A61B 2017/308; A61B 5/6865; A61B 2017/0237; A61B 2017/0243; A61F 2/2478
See application file for complete search history.

(56) References Cited

U.S. PATENT DOCUMENTS

| | | |
|---|---|---|
| 4,007,743 A | 12/1977 | Blake |
| 4,313,448 A | 2/1982 | Stokes |
| 4,357,946 A | 11/1982 | Dutcher et al. |
| 4,991,578 A | 2/1991 | Cohen |
| 5,139,033 A | 8/1992 | Everett |
| 5,154,709 A * | 10/1992 | Johnson ............. A61B 18/1402 604/35 |
| 5,246,014 A | 9/1993 | Williams et al. |
| 5,295,958 A | 3/1994 | Shturman |
| 5,336,252 A * | 8/1994 | Cohen .................. A61N 1/0587 606/129 |
| 5,464,447 A | 11/1995 | Fogarty et al. |
| 5,482,037 A | 1/1996 | Borghi |
| 5,484,445 A | 1/1996 | Knuth |
| 5,522,875 A | 6/1996 | Gates et al. |
| 5,540,648 A * | 7/1996 | Yoon .................. A61B 17/3403 600/102 |
| 5,553,612 A | 9/1996 | Lundback |
| 5,575,814 A | 11/1996 | Giele et al. |
| 5,716,391 A | 2/1998 | Grandjean |
| 5,716,392 A | 2/1998 | Bourgeois et al. |
| 5,727,569 A * | 3/1998 | Benetti .................. A61B 17/00 128/898 |
| 5,755,697 A | 5/1998 | Jones et al. |
| 5,766,164 A * | 6/1998 | Mueller ............. A61B 17/3403 606/15 |
| 5,792,217 A | 8/1998 | Camps et al. |
| 5,810,884 A | 9/1998 | Kim |
| 5,827,216 A | 10/1998 | Igo et al. |
| 5,830,224 A | 11/1998 | Cohn et al. |
| 5,865,730 A | 2/1999 | Fox et al. |
| 5,868,770 A * | 2/1999 | Rygaard ................. A61B 17/11 606/167 |
| 5,871,352 A | 2/1999 | Schroeppel |
| 5,871,528 A | 2/1999 | Camps et al. |
| 5,897,584 A | 4/1999 | Herman |
| 5,902,331 A | 4/1999 | Bonner et al. |
| 5,902,234 A | 5/1999 | Thompson et al. |
| 5,961,440 A | 10/1999 | Schweich, Jr. et al. |
| 5,972,013 A | 10/1999 | Schmidt |
| 6,010,476 A | 1/2000 | Saadat |
| 6,010,526 A | 1/2000 | Sandstrom et al. |
| 6,045,497 A | 4/2000 | Schweich et al. |
| 6,050,936 A | 4/2000 | Schweich, Jr. et al. |
| 6,059,715 A | 5/2000 | Schweich, Jr. et al. |
| 6,059,719 A * | 5/2000 | Yamamoto ......... A61B 1/00059 600/104 |
| 6,080,175 A | 6/2000 | Hogendijk |
| 6,080,182 A | 6/2000 | Shaw et al. |
| 6,125,852 A | 10/2000 | Stevens et al. |
| 6,132,456 A | 10/2000 | Sommer et al. |
| 6,152,918 A | 11/2000 | Padilla et al. |
| 6,155,968 A | 12/2000 | Wilk |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,166,684 A | 12/2000 | Yoshikawa et al. |
| 6,185,464 B1 | 2/2001 | Bonner et al. |
| 6,193,652 B1 | 2/2001 | Berky et al. |
| 6,219,579 B1 | 4/2001 | Bakels et al. |
| 6,231,518 B1 | 5/2001 | Grabek et al. |
| 6,258,021 B1 | 7/2001 | Wilk |
| 6,260,552 B1 | 7/2001 | Mortier et al. |
| 6,406,420 B1 | 6/2002 | McCarthy et al. |
| 6,478,029 B1 * | 11/2002 | Boyd ............... A61B 17/00234 128/898 |
| 6,494,211 B1 * | 12/2002 | Boyd ............... A61B 17/00234 128/898 |
| 6,494,825 B1 | 12/2002 | Talpade |
| 6,511,416 B1 | 1/2003 | Green et al. |
| 6,572,529 B2 | 6/2003 | Wilk |
| 6,616,684 B1 | 9/2003 | Vidlund et al. |
| 6,623,508 B2 | 9/2003 | Shaw et al. |
| 6,705,988 B2 | 3/2004 | Spence et al. |
| 6,709,382 B1 | 3/2004 | Horner |
| 6,723,038 B1 | 4/2004 | Schroeder et al. |
| 6,746,471 B2 | 6/2004 | Mortier et al. |
| 6,776,754 B1 | 8/2004 | Wilk |
| 6,808,488 B2 | 10/2004 | Mortier |
| 6,859,662 B2 | 2/2005 | Bombardini |
| 6,890,295 B2 | 5/2005 | Michels et al. |
| 7,146,225 B2 | 12/2006 | Guenst et al. |
| 7,326,177 B2 | 2/2008 | Williamson |
| 7,373,207 B2 * | 5/2008 | Lattouf ............. A61B 17/00234 600/16 |
| 7,390,329 B2 | 6/2008 | Westra et al. |
| 7,431,691 B1 | 10/2008 | Wilk |
| 7,507,200 B2 * | 3/2009 | Okada .................... A61B 1/012 600/104 |
| 7,637,924 B2 | 12/2009 | Gifford et al. |
| 7,722,523 B2 | 5/2010 | Mortier et al. |
| 7,753,923 B2 | 7/2010 | St. Goar et al. |
| 7,766,816 B2 | 8/2010 | Chin et al. |
| 7,785,248 B2 | 8/2010 | Annest et al. |
| 7,842,015 B2 * | 11/2010 | Chachques .......... A61N 1/0573 604/174 |
| 7,942,854 B1 | 5/2011 | Von Oepen et al. |
| 8,066,766 B2 | 11/2011 | To et al. |
| 8,123,668 B2 | 2/2012 | Annest et al. |
| 8,268,009 B2 | 9/2012 | Teitelbaum et al. |
| 8,394,008 B2 | 3/2013 | Annest et al. |
| 8,425,402 B2 | 4/2013 | Annest et al. |
| 8,449,442 B2 | 5/2013 | Annest et al. |
| 8,491,455 B2 | 7/2013 | Annest et al. |
| 8,506,474 B2 | 8/2013 | Chin et al. |
| 8,636,639 B2 | 1/2014 | Annest et al. |
| 8,968,175 B2 | 3/2015 | Annest et al. |
| 8,979,750 B2 | 3/2015 | Bladel et al. |
| 8,986,189 B2 | 3/2015 | Chin et al. |
| 9,039,594 B2 | 5/2015 | Annest et al. |
| 9,044,231 B2 | 6/2015 | Annest et al. |
| 9,095,363 B2 | 8/2015 | Bladel et al. |
| 9,119,720 B2 | 9/2015 | Chin et al. |
| 9,173,711 B2 | 11/2015 | Butler et al. |
| 9,173,712 B2 | 11/2015 | Annest et al. |
| 9,211,115 B2 | 12/2015 | Annest et al. |
| 9,259,319 B2 | 2/2016 | Chin et al. |
| 9,402,722 B2 | 8/2016 | Annest et al. |
| 9,486,206 B2 | 11/2016 | Annest et al. |
| 9,526,618 B2 | 12/2016 | Chin et al. |
| 2001/0025171 A1 | 9/2001 | Mortier et al. |
| 2001/0041821 A1 | 11/2001 | Wilk |
| 2002/0058855 A1 | 5/2002 | Schweich, Jr. et al. |
| 2002/0077524 A1 | 6/2002 | Schweich, Jr. et al. |
| 2002/0077655 A1 | 6/2002 | Frova |
| 2002/0120298 A1 | 8/2002 | Kramer et al. |
| 2002/0123768 A1 | 9/2002 | Gilkerson et al. |
| 2002/0139377 A1 | 10/2002 | Ekvall et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2002/0198563 A1 | 12/2002 | Gainor et al. |
| 2003/0032979 A1 | 2/2003 | Mortier et al. |
| 2003/0163165 A1 | 8/2003 | Bornzin et al. |
| 2003/0166992 A1 | 9/2003 | Schweich, Jr. et al. |
| 2003/0181928 A1 | 9/2003 | Vidlund et al. |

(56) References Cited

U.S. PATENT DOCUMENTS

| | | |
|---|---|---|
| 2003/0181951 A1 | 9/2003 | Cates |
| 2003/0212446 A1 | 11/2003 | Kaplan et al. |
| 2003/0220587 A1 | 11/2003 | Swenson |
| 2003/0233022 A1 | 12/2003 | Vidlund et al. |
| 2004/0064143 A1 | 4/2004 | Hicken et al. |
| 2004/0082837 A1 | 4/2004 | Willis |
| 2004/0088035 A1* | 5/2004 | Guenst ............... A61N 1/0587 607/131 |
| 2004/0138526 A1 | 7/2004 | Guenst |
| 2004/0143153 A1 | 7/2004 | Sharrow |
| 2004/0167374 A1 | 8/2004 | Schweich |
| 2004/1647580 | 8/2004 | Mann et al. |
| 2004/0225304 A1 | 11/2004 | Vidlund et al. |
| 2004/0267306 A1 | 12/2004 | Blaeser et al. |
| 2005/0065506 A1 | 3/2005 | Phan |
| 2005/0075723 A1 | 4/2005 | Schroeder et al. |
| 2005/0096498 A1 | 5/2005 | Houser et al. |
| 2005/0137688 A1 | 6/2005 | Salahieh et al. |
| 2005/0143620 A1 | 6/2005 | Mortier et al. |
| 2005/0149115 A1 | 7/2005 | Roue et al. |
| 2005/0192599 A1 | 9/2005 | Demarais |
| 2005/0215851 A1 | 9/2005 | Kim et al. |
| 2005/0288613 A1 | 12/2005 | Heil, Jr. |
| 2006/0004408 A1 | 1/2006 | Morris et al. |
| 2006/0079736 A1 | 4/2006 | Chin et al. |
| 2006/0135962 A1 | 6/2006 | Kick et al. |
| 2006/0131238 A1 | 7/2006 | Hall |
| 2006/0161040 A1 | 7/2006 | McCarthy et al. |
| 2006/0161238 A1 | 7/2006 | Hall |
| 2006/0167416 A1 | 7/2006 | Mathis et al. |
| 2006/0178550 A1 | 8/2006 | Jenson |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1 | 12/2006 | Speziali |
| 2007/0005018 A1 | 1/2007 | Tkebuchava |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073274 A1 | 3/2007 | Chin et al. |
| 2007/0112244 A1 | 5/2007 | McCarthy et al. |
| 2007/0161846 A1 | 7/2007 | Nikotic et al. |
| 2007/0203503 A1 | 8/2007 | Salahieh et al. |
| 2007/0265658 A1 | 11/2007 | Nelson et al. |
| 2007/0287884 A1 | 12/2007 | Schena |
| 2008/0058650 A1 | 3/2008 | Saadat et al. |
| 2008/0082132 A1 | 4/2008 | Annest et al. |
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287165 A1 | 11/2009 | Drapeau et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0030142 A1* | 2/2010 | Onishi ............... A61M 25/1036 604/103.07 |
| 2010/0057000 A1 | 3/2010 | Melsheimer et al. |
| 2010/0268020 A1 | 10/2010 | Chin et al. |
| 2011/0160750 A1 | 6/2011 | Annest et al. |
| 2011/0270191 A1 | 11/2011 | Paul et al. |
| 2011/0301622 A1* | 12/2011 | Oren ............... A61B 17/0483 606/145 |
| 2012/0130191 A1* | 5/2012 | Pribanic ............ A61B 17/3423 600/208 |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2014/0350417 A1 | 11/2014 | Bladel et al. |
| 2015/0066139 A1 | 3/2015 | Bladel et al. |
| 2015/0238182 A1 | 8/2015 | Annest et al. |
| 2016/0022422 A1 | 1/2016 | Annest et al. |
| 2016/0030026 A1 | 2/2016 | Bladel et al. |
| 2016/0089132 A1 | 3/2016 | Butler et al. |
| 2016/0095600 A1 | 4/2016 | Annest et al. |
| 2016/0120648 A1 | 5/2016 | Chin et al. |
| 2016/0206427 A1 | 7/2016 | Annest et al. |
| 2016/0262891 A1 | 9/2016 | Chin et al. |
| 2016/0338835 A1 | 11/2016 | Bladel et al. |

FOREIGN PATENT DOCUMENTS

| | | |
|---|---|---|
| WO | 20002/04064 A1 | 1/2002 |
| WO | 2002/30335 A2 | 4/2002 |
| WO | 2003/032818 A3 | 4/2003 |
| WO | 2004-043267 A2 | 5/2004 |
| WO | 2005/092203 A1 | 10/2005 |
| WO | 2006/044467 A2 | 4/2006 |
| WO | 2007/022519 A2 | 2/2007 |
| WO | 2013-049761 A1 | 4/2013 |

OTHER PUBLICATIONS

International Search Report and Written Opinion of PCT Application No. PCT/US06/32663, dated Jul. 31, 2007, 5 pages.

International Search Report and Written Opinion of PCT Application No. PCT/US08/64255, dated Sep. 29, 2008, 13 pages.

International Search Report and Written Opinion of PCT Application No. PCT/US08/78810, dated Feb. 12, 2009,9 pages.

International Search Report and Written Opinion of PCT Application No. PCT/US09/51288, dated Sep. 15, 2009, 7 pages.

International Search Report and Written Opinion of PCT Application No. PCT/US12/58074, dated Mar. 13, 2013, 18 pages.

International Search Report and Written Opinion of PCT Application No. PCT/US2005/036690, dated Jul. 9, 2007, 6 pages.

International Search Report and Written Opinion of PCT/US2012/058106, dated Nov. 26, 2012, 14 pages.

International Search Report and Written Opinion of PCT/US2012/58176, dated Jan. 8, 2013, 19 pages.

International Search Report and Written Opinion of PCT/US2012/058182, dated Mar. 1, 2013, 19 pages.

International Report on Patentability of PCT/US2012/058176 dated Apr. 10, 2014, 11 pages.

European Examination Report of EP Patent Application 12837466.7 dated Jun. 6, 2016, 14 pages.

International Search Report and Written Opinion of PCT/US2014/038834 dated Oct. 16, 2014, 16 pages.

International Report on Patentability of PCT/US2014/038834 dated Dec. 3, 2015, 11 pages.

EP 14840114.4 received an Extended European Search and Report dated Jun. 14, 2017, all pages.

European Examination Report of EP Patent Application 05810316.9 dated Mar. 10, 2009, 6 pages.

Extended European Examination Report of EP Patent Application 06802038.7 dated Nov. 12, 2013, 13 pages.

Office Action of EP Patent Application 06802038.7 dated Sep. 11, 2014, 4 pages.

International Report on Patentability of PCT-US2012-058074 dated Apr. 10, 2014, 8 pages.

USPTO—STIC Search Results—NPL (Dec. 11, 2014).

USPTO—STIC Search Results—Patents (Dec. 11, 2014).

International Search Report and Written Opinion of PCT Application No. PCT-US2014-053209 dated Mar. 2, 2015, 18 pages.

* cited by examiner

CARDIAC TISSUE ANCHORING DEVICES, METHODS, AND SYSTEMS FOR TREATMENT OF CONGESTIVE HEART FAILURE AND OTHER CONDITIONS

CROSS-REFERENCE TO RELATED APPLICATIONS

This application claims priority to Provisional U.S. patent application Ser. No. 61/872,556 filed Aug. 30, 2013, entitled "Cardiac Tissue Anchoring Devices, Methods, and Systems for Treatment of Congestive Heart Failure and Other Conditions," the entire disclosure of which is hereby incorporated by reference, for all purposes, as if fully set forth herein.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF SUMMARY OF THE INVENTION

The embodiments described herein may be used for reducing the distance between a region along the septum and a region of an external wall of the left ventricle of a heart in a less or minimally invasive manner. In one aspect, a heart tissue gripping device includes a body portion, an elongate shaft, a tissue gripping member, and a coupling. The body portion may be gripped by a user to allow the user to control the device so that one or more components of the device, such as the tissue gripping member and elongate shaft, may be inserted through an incision in a body and positioned adjacent a surface of the heart. A proximal end of the elongate shaft is coupled with the body portion and a distal end of the elongate shaft is coupled with the tissue gripping member. The tissue gripping member is configured to releasably attach to tissue of the heart surface and the coupling allows a surgical device (e.g., a catheter shaft and/or tissue penetrating device) to be releasably attached to the tissue gripping member to allow said device to access the tissue of the heart surface.

In another aspect, a method for penetrating tissue of a heart wall includes positioning a tissue gripping member of a heart tissue gripping device adjacent a surface of the heart and gripping tissue of the heart surface with the tissue gripping member to releasably attach the tissue gripping member to the heart surface. The method also includes attaching a tissue penetrating device to a coupling of the tissue gripping member and penetrating the tissue of the heart wall with the tissue penetrating device. The method further includes detaching the tissue penetrating device from the coupling of the tissue gripping member.

In another aspect, a method for treating a heart includes attaching a device to a surface of a first wall of the heart by gripping the heart tissue with a tissue gripping member of the device. The tissue of the first wall of the heart is penetrated with a tissue penetrating device and a tension member is inserted through the first wall of the heart and through a second wall of the heart. A chamber (i.e., left ventricle) separates the first wall and second wall. A first anchor is positioned in engagement with the second wall. The first anchor is coupled with or otherwise attached to the tension member. The device is then detached from the surface of the first wall of the heart by releasing the heart tissue with the tissue gripping member. A second anchor is positioned in engagement with the first wall of the heart. The second anchor is slidably coupled with the tension member to allow the second anchor to slide proximally and distally along a length of the tension member. An anchor force is then applied between the tension member and the second anchor so that the first anchor urges the second wall toward the first wall and the second anchor urges the first wall toward the second wall. The second anchor is secured to the tension member to restrict proximal movement of the second anchor along the tension member. In some embodiments, the first wall and the second wall are brought into engagement via the anchor force applied between the tension member and the second anchor.

BRIEF DESCRIPTION OF THE DRAWINGS

The present invention is described in conjunction with the appended figures.

Figure 1:
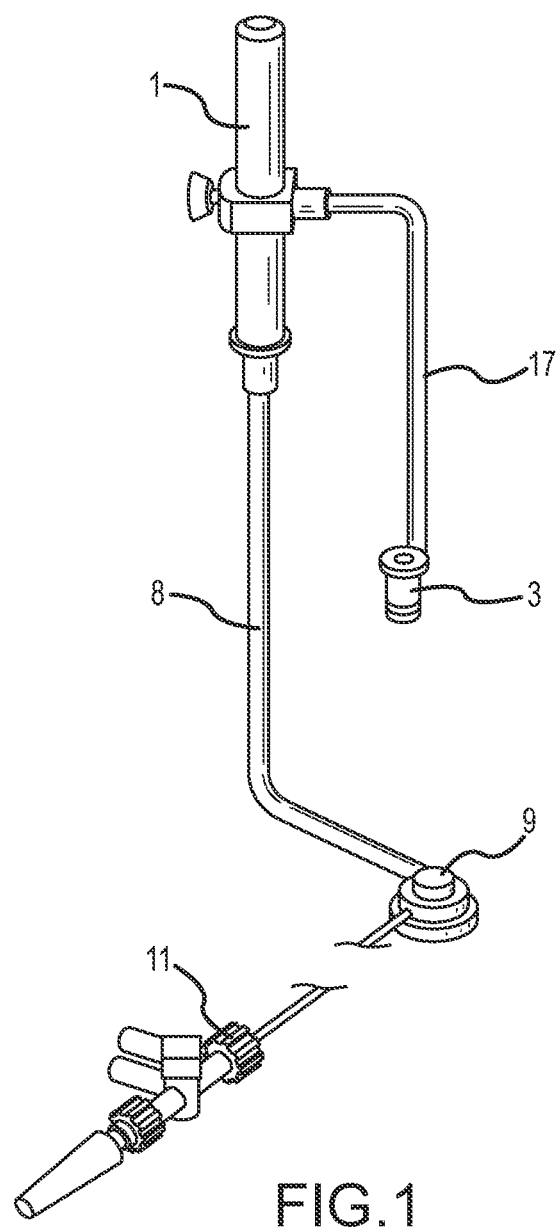
FIG. 1 illustrates a schematic perspective view of a tissue anchoring device that may be used in performing procedures on the heart.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction.

In treating congestive heart failure and/or performing other operations on the heart, it may be important to penetrate the heart with a needle or other device. For example, treatment of congestive heart failure often involves penetrating an external wall and/or septal wall of the heart with a needle in order to allow a guidewire and tension member/tether to be passed through the external and/or septal wall. Heart anchors may then be engaged with the septal and/or external walls by tensioning the tension member that is coupled with the heart anchors. Further tensioning of the tension member may draw the septal and external walls together, and one or more of the anchors may be secured to the tension member to lock or maintain the heart walls in an engaged position.

In performing the above congestive heart failure treatment, the needle is often penetrated through tough scar tissue. The needle is also often controlled by a physician from outside the heart. Penetrating the needle from outside the heart and through the tough scar tissue may be difficult due to the relatively tough and hard characteristic of the tissue. For example, the scar tissue often resists puncturing and tends to move or displace as the needle is pressed against and into the tissue. To remedy this problem, a heart tissue anchoring or gripping device as described herein (hereinafter heart tissue gripping device) may be used to grip and secure the heart tissue. The heart tissue gripping device is configured to releasably attach to the heart surface and to hold or secure the heart tissue in order to allow a needle or other device to penetrate through the tissue, or to otherwise perform some surgical procedure thereon. Stated differently, the heart tissue gripping device is used to grip onto the heart surface and to provide a counterforce to the force of the needle or other device pushing against the heart.

As described above, after the needle penetrates the heart tissue, a tension member is typically inserted through the heart wall penetration. The heart tissue gripping device may then be removed from the heart surface and/or from the body of the patient. In removing the heart tissue gripping device, however, it is often desirable to grip or hold the tension member to provide hemostasis to the heart wall penetration and/or prevent the tether from migrating within the body. The heart tissue gripping device described herein includes a fastening mechanism that is used to grip or grab the tension member in order to allow the heart tissue gripping device to be removed from the body while providing hemostasis to the heart wall penetration.

The fastening mechanism may be preloaded or coupled with the heart tissue gripping device prior to insertion of the heart tissue gripping device into the body. After the needle penetrates through the heart tissue and the tension member is passed through the heart wall, the fastening mechanism may be detached from the heart tissue gripping device and placed over or adjacent the tension member to allow the fastening mechanism to grip or fasten with the tension member.

In one embodiment, the fastening mechanism is a wire noose that may be placed into an annular channel of the heart tissue gripping device. To detach the wire noose from the heart tissue gripping device, the noose diameter may be increased, such as by releasing tension on the wire, and the wire noose may be removed from the annular channel. The wire noose may then be moved axially downward relative to the heart tissue gripping device and placed over and around the tension member. The wire noose may be cinched around the tension member to grip or fasten with the tension member. The cinched noose provides hemostasis to the heart wall since the cinched noose is positioned adjacent the heart wall penetration. The heart tissue gripping device may then be removed from the body with the wire noose fastened with the tension member.

Although the noose is described herein as a wire noose, the noose material is not limited to wires. For example, other types of lace may be used for the noose. The lace materials may include fabric, polymers, metals, and the like. These materials may be woven or braided to form the lace that is used for the noose. The term wire noose as used herein is meant to encompass all of these materials. The use of metal wires, however, may be preferred because metal materials allow the wire to be pushed or compressed to some degree to increase the noose diameter. This may facilitate in removing or uncoupling the wire from the heart tissue gripping device.

Having described several features of the heart tissue gripping device generally, additional features and uses of the heart tissue gripping device will be realized in the disclosure of the several drawings below.

FIG. 1 illustrates a heart tissue gripping device that is useful in treating congestive heart failure and/or other heart conditions. The heart tissue gripping device includes a body portion 1 that may be gripped by a user to allow the user to control the device. For example, a user may grip body portion 1 to move a distal end of the device, and/or one or more components coupled therewith (e.g., tissue gripping member 9), through an incision in the body in treating congestive heart failure. The one or more components may be moved until the components are adjacent a surface of the heart where treatment is to be provided.

An elongate shaft 8 is coupled at a proximal end with body portion 1. A distal end of the elongate shaft 8 is coupled with a tissue gripping member 9 that is used to releasably attach or fasten the device with the heart surface. In some embodiments, the elongate shaft 8 may be malleable to allow a user to bend the elongate shaft 8 into a configuration that allows the tissue gripping member 9 to be inserted through an incision in the body and easily moved within the body to a desired position on the heart. For example, the tissue gripping member 9 is often inserted through a subxiphoid incision and subsequently moved to a position adjacent the heart that is relatively remote or distant from the subxiphoid incision. The treatment position is also typically substantially offset from an axis of the elongate shaft. The malleable elongate shaft 8 allows the tissue gripping member 9 to be easily inserted through the subxiphoid incision and moved to a position where treatment is desired. The malleable elongate shaft 8 may further allow a single device size or type to be adapted for multiple individuals. The elongate shaft 8 is sufficiently rigid to resist bending as the tissue gripping member 9 is inserted through the subxiphoid incision and moved within the body to the selected treatment site of the heart. The malleable elongate shaft 8 may be reconfigured to include one or multiple bends (up to or exceeding 90°) and/or to include one or more curved configurations that enables easy insertion thought an incision and movement within the body.

The tissue gripping member 9 is configured to releasably attach to the tissue of the heart surface. To attach to the heart tissue, the tissue gripping member 9 may include a suction device or component. An example of a suction device that may be used to releasably couple with heart tissue is described in U.S. application Ser. No. 13/632,103, filed Sep. 30, 2012 and entitled "Remote Pericardial Hemostasis for Ventricular Access and Reconstruction or Other Organ Therapies," and U.S. application Ser. No. 10/283,794, filed Oct. 30, 2002 and entitled "Methods and Apparatus for Accessing and Stabilizing an Area of the Heart," the entire disclosures of which are incorporated by reference herein. In some embodiments, the tissue gripping member 9 may include mechanical fastening components that are used to releasably attach to or otherwise grip the heart tissue.

In the embodiment shown in FIG. 1, tissue gripping member 9 is fluidly coupled with a vacuum component 11. As shown in greater detail herein below, the tissue gripping member 9 may include a cavity having an access port that allows the vacuum component 11 to apply suction to the tissue gripping member 9. The heart tissue gripping device also includes a second shaft 17 that is coupled at a proximal end with the body portion 1. A distal end of the second shaft 17 is coupled with the cannular member 3. The cannular member 3 includes a lumen or catheter shaft through which one or more devices may be inserted. The second shaft 17 is also malleable in order to allow the cannular member 3 to be moved and axially aligned with an axis of the tissue gripping member 9. In use, the cannular member 3 is positioned axially above the tissue gripping member 9 and outside the body while the tissue gripping member 9 is fastened with the heart surface.

In some embodiments, the cannular member 3 may be a cannula or trocar component that is positioned within an incision in the body, such as within an incision between ribs of the patient. Operational devices, such as a needle, access catheter, and the like may be inserted through the cannular member 3 and positioned adjacent or coupled with tissue gripping member 9. The cannular member 3 helps to axially align the needle or other devices with the tissue gripping member 9 to allow such devices to easily couple with and/or access the tissue gripping member 9. In this manner, the tissue gripping member 9 may be inserted through the subxiphoid incision and positioned adjacent the heart while other devices or instruments are inserted through an incision axially above the tissue gripping member 9, such as within the incision between the ribs. The incision axially above the tissue gripping member 9 may allow such instruments or devices to have direct or straight-line access to the tissue gripping member 9 and treatment site of the heart.

Figure 2A:
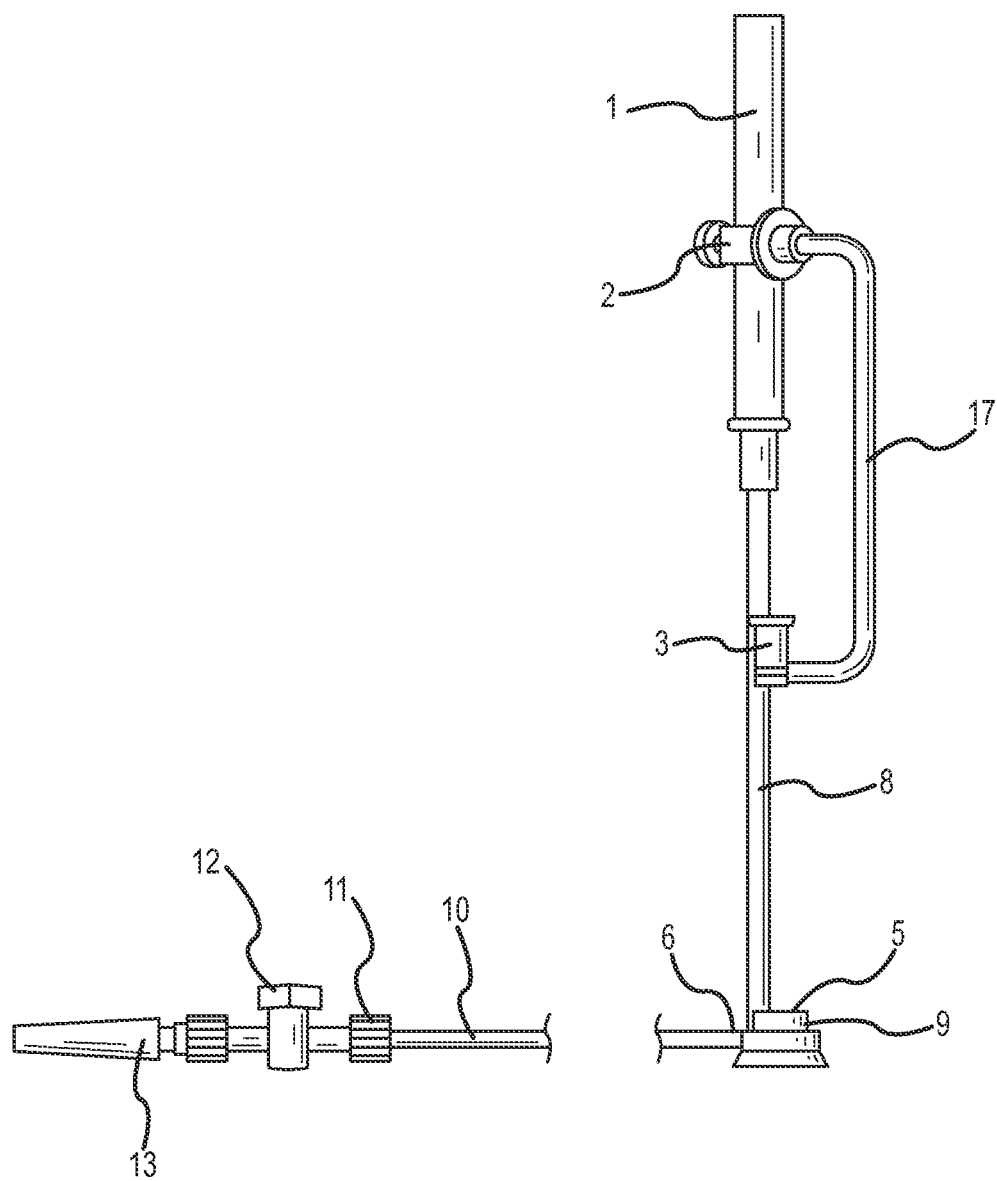
FIG. 2A illustrates a schematic side view of the tissue anchoring device of FIG. 1.

FIG. 2A illustrates a side profile view of the heart tissue gripping device of FIG. 1. As shown in FIG. 2A, body portion 1 is coupled with a proximal end of elongate shaft 8 while the distal end of the elongate shaft 8 is coupled with the tissue gripping member 9. The second shaft 17 is also coupled at a proximal end with body portion 1 while a distal end of the second shaft 17 is coupled with the cannular member 3. Tubing 10 connects the vacuum component 11 with the tissue gripping member 9. The tissue gripping member 9 includes an access port 6 that is fluidly coupled with the tubing 10 of vacuum component 11. The vacuum component 11 includes a control valve 12 that allows a user to control the application of the vacuum so as to attach and detach the tissue gripping member 9 with the heart tissue. The vacuum component 11 may be coupled with any vacuum source known in the art via vacuum port or connection 13.

In operation, body portion 1 may be gripped by a user to control the insertion of tissue gripping member 9 through the body and adjacent the heart surface. When the tissue gripping member 9 is positioned at a desired treatment site of the heart, control valve 12 may be used to apply a vacuum pressure to tissue gripping member 9 and thereby attach the tissue gripping member 9 to the heart surface. A tissue penetrating device (e.g. needle) or other device may then be inserted through cannular member 3 and coupled with tissue gripping member 9 to allow the tissue penetrating device to penetrate or puncture the heart tissue, or to allow another surgical procedure to be performed. The tissue gripping member 9 and heart tissue gripping device allow the heart tissue to be easily penetrated, or a surgical procedure to be performed thereon, by securing, holding, or otherwise maintain the heart tissue in position as the tissue is penetrated or the surgical procedures performed. The tissue gripping member 9 and heart tissue gripping device provide a counterforce to any a force exerted on the heart tissue by the surgical instrument. After the procedure is performed, control valve 12 may be used to remove the vacuum pressure and thereby allow tissue gripping member 9 to be removed or detached from the heart surface.

To couple the surgical instruments with the heart tissue gripping device, the tissue gripping member 9 may include an access port 5 that includes a coupling for releasably attaching the surgical device with the tissue gripping member 9. The access port 5 further allows the surgical device to access the tissue of the heart surface.

Figure 2B:
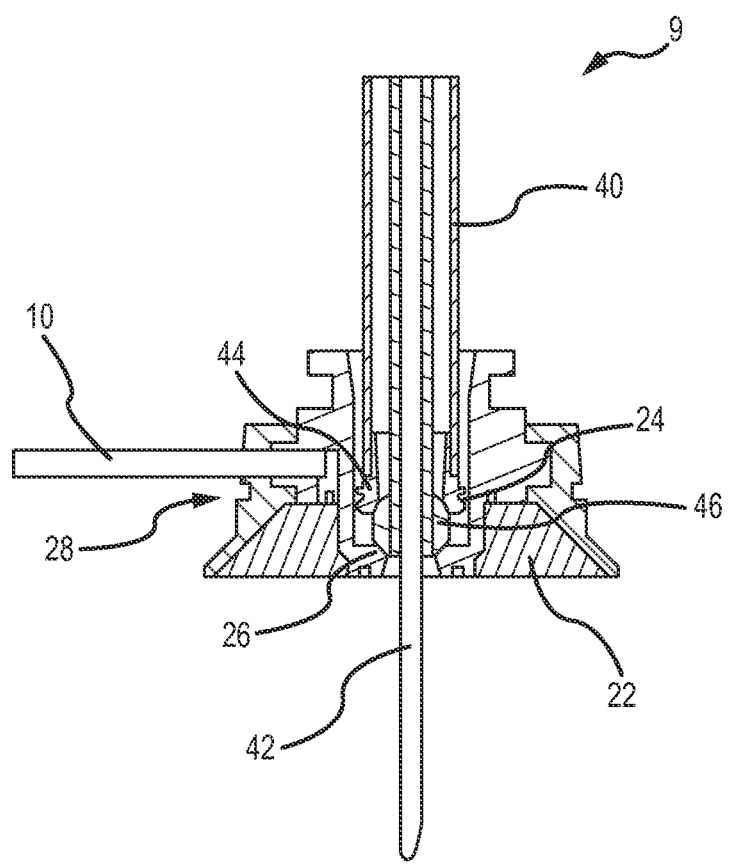
FIG. 2B illustrates a side cross sectional view of a gripping member of the tissue anchoring device of FIG. 1.
Figure 2C:
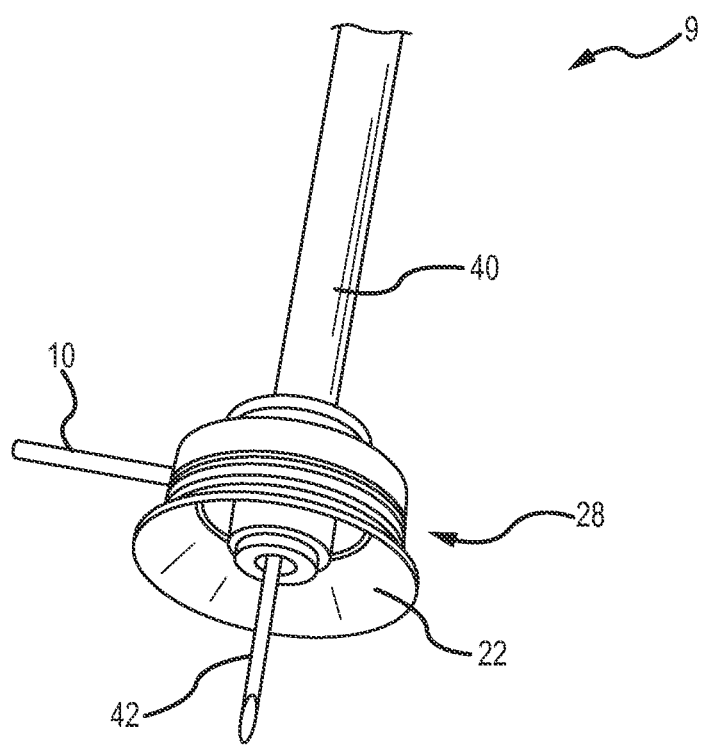
FIG. 2C illustrates a perspective view of the gripping member of FIG. 2B.

FIGS. 2B and 2C illustrate the tissue gripping member 9 in greater detail. FIGS. 2B and 2C further illustrate a surgical device coupled with the tissue gripping member 9. FIG. 2B is a cross-sectional view of the tissue gripping member 9 and illustrates various internal components of the tissue gripping member 9. The surgical device illustrated in FIGS. 2B and 2C is a tissue penetrating device 40 that includes a needle 42 that is used to penetrate through a central lumen of tissue gripping member 9 and into the heart tissue. Exemplary embodiments of tissue penetrating devices that may be coupled with the tissue gripping member 9 are described in U.S. application Ser. No. 14/282,849, filed May 20, 2014 and entitled "Cardiac Tissue Penetrating Devices, Methods, and Systems for Treatment of Congestive Heart Failure and Other Conditions," the entire disclosure of which is incorporated by reference herein.

To couple the tissue penetrating device 40 with the tissue gripping member 9, tissue gripping member 9 includes a coupling 24, which in the illustrated embodiment is a threaded aperture. A distal end of the tissue penetrating device 40 is threaded 44 to allow the tissue penetrating device 40 to be removably coupled with tissue gripping member 9. In other embodiments, the coupling 24 of tissue gripping member 9 may be a ball and socket type joint and a distal end of the tissue penetrating device 40 may include a ball that may be inserted into the ball and socket joint to couple the tissue penetrating device 40 with the tissue gripping member 9. In some embodiments, a distal end of the aperture of tissue gripping member 9 may have a spherical or radiused contour 26 that corresponds with a ball 46 of tissue penetrating device 40. This contour 26 may allow the tissue penetrating device 40 to be rotated or moved relative to tissue gripping member 9 by some degree, such as up to about 15° from an axis of tissue gripping member 9.

Although the coupling is illustrated as a centrally positioned threaded aperture, the coupling may be positioned elsewhere and/or include other attachment mechanisms. For example, the coupling may be positioned on the side of the tissue gripping member and include various clips, clamps, threads, locks, cams, and the like to couple the tissue penetrating device 40, or other device, with the tissue gripping member 9. Further, in some embodiments, the coupling may be a component that is separate from and attached to the tissue gripping member 9.

As shown in FIG. 2C, tissue gripping member 9 may be bell or hemispherically shaped object and may have a hollow cavity or inner surface 22. The inner surface 22 may have an access port that fluidly couples with tubing 10 of vacuum component 11 to allow a vacuum pressure to be applied to the surface of the heart and thereby fasten tissue gripping member 9 with the heart tissue and surface. The tissue gripping member 9 may also include an annular groove 28 within which a fastening component (see FIGS. 3A & B) may be positioned. The fastening component may be "preloaded" with the tissue gripping member 9, or in other words may be coupled with the tissue gripping member 9 prior to insertion of the tissue gripping member within the body. Although tissue gripping member 9 is shown as a bell or hemispherically shaped object, the tissue gripping member 9 may have various other shapes, such as a U-shape, L-shape, box shape, and the like. Some of these shapes may facilitate in uncoupling the tissue gripping member 9 and tether or tension member.

Figure 3A:
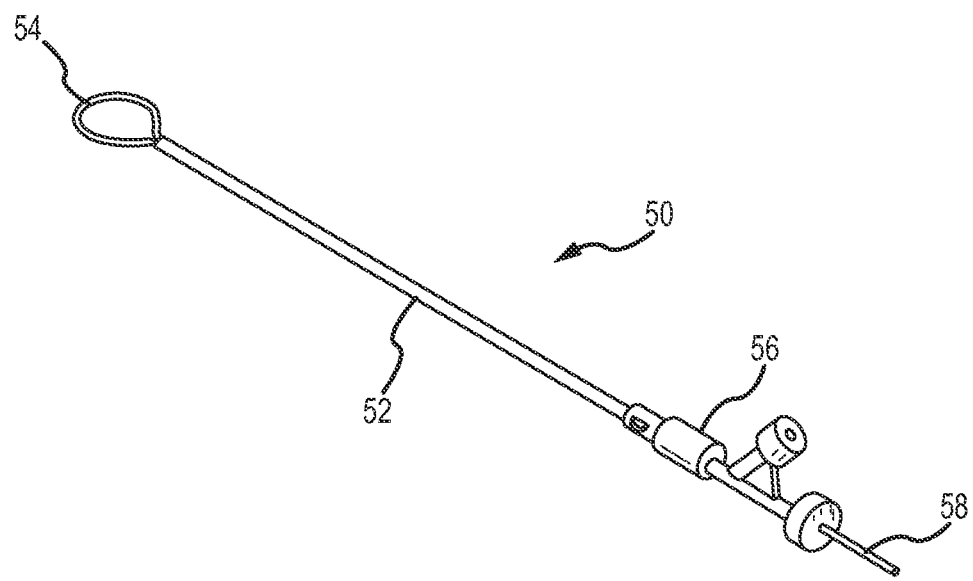
FIG. 3A illustrates a schematic perspective view of a fastening device that may be used with the tissue anchoring device of FIG. 1.
Figure 3B:
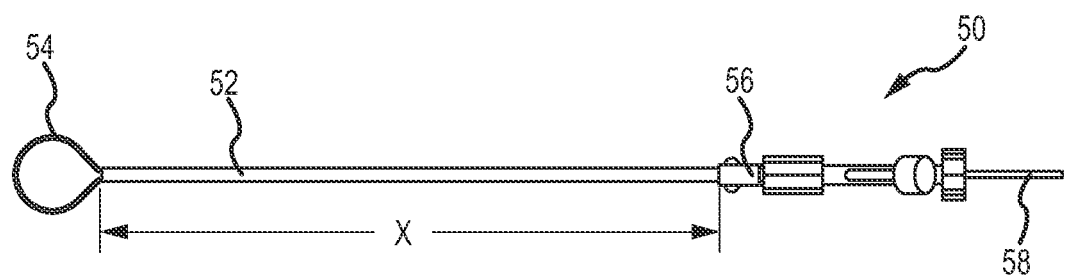
FIG. 3B illustrates a schematic side view of the fastening device of FIG. 3A.

FIGS. 3A and 3B illustrate an embodiment of a fastening component 50. Fastening component 50 includes a shaft or catheter body 52 having a lumen between a proximal and distal end. A wire 58 is inserted through the lumen of catheter body 52 and forms a noose 54 at the distal end of catheter body 52. The noose 52 may be positioned within the annular groove 28 of tissue gripping member 9. The diameter of noose 54 may be increased to uncouple the noose 54 from the annular groove 28 of tissue fastening member 9. To increase the diameter of noose 54, wire 58 may be pushed through the lumen of catheter body 52 and/or a proximal end of fastening component 50 may be pulled so that the tissue gripping member 9 presses against noose 54 to open or expand the noose. Similarly, wire 58 may be tensioned or pulled to decrease the diameter of the noose 54 and thereby cinch the noose 54 or around a tension member/tether, heart tissue, or other object (not shown).

The catheter body 52 may have a length X that allows the distal end of the fastening component 50 to be positioned outside the body while the noose 54 is positioned around tissue gripping member 9 adjacent the heart surface. The proximal end of fastening component 50 may include a lock mechanism 56 that may lock the wire 58 in position relative to catheter body 52. For example, in using the fastening component 50, a user may position the noose 54 around a tension member and pull or tension wire 58 to cinch the noose 54 around the tension member. The user may then operate lock mechanism 56 to lock the wire 58 with the noose 54 cinched around the tension member. In this manner, the user is not required to maintain tension on wire 58 in order to keep the noose 54 cinched around the tension member or other object. The lock mechanism 56 may be a rotatable component that presses against the wire 58 to lock and unlock the wire 58.

Figure 4A:
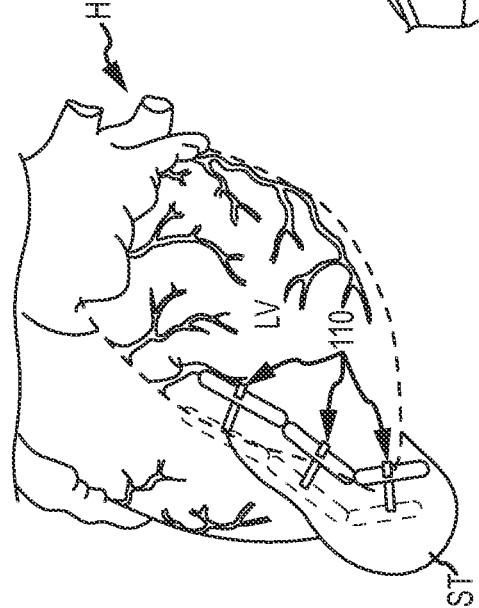
FIG. 4A illustrates a reconstructed left ventricle using a series of implanted anchors so as to mitigate the deleterious effects of congestive heart failure.
Figure 4B:
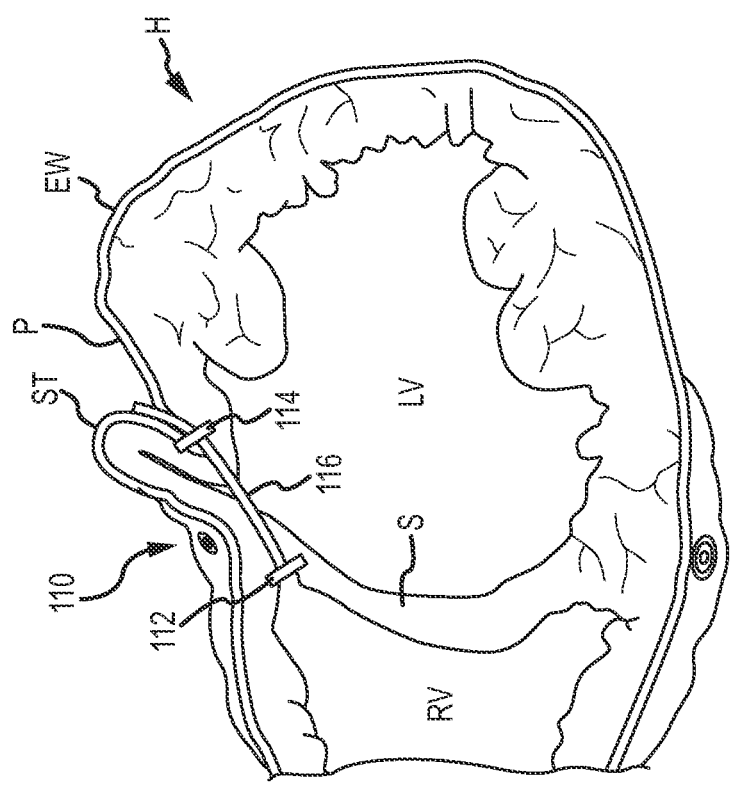
FIG. 4B illustrates a cross-sectional view of the heart of FIG. 4A, showing a reduction in the size of the left ventricle effected by one of the implants.

Referring now to FIGS. 4A-5D, a procedure for treating congestive heart failure using a heart tissue gripping device 430 as described herein is illustrated. Specifically, FIGS. 4A and 4B illustrate a series of implants 110 implanted in a heart H so as to decrease a cross-section of a left ventricle LV. Each implant 110 generally includes a first anchor 112, a second anchor 114, and a tension member 116 coupling the anchors together. Tension in the tension member 116 is transferred from the anchors, 112 and 114, to the septum S and the external wall EW bordering the left ventricle LV so as to bring these structures into engagement, thereby effectively excluding a region of scar tissue ST from the left ventricle. In many embodiments described herein, implant 110 will be deployed by penetrating the external wall EW and septum S via a pericardium P of the heart H, and also by accessing a right ventricle RV via a right atrium. Anchors deployed within a right ventricle and/or in engagement with the septum S may sometimes be referred to herein as septal anchors, while anchors deployed along the external wall EW of the left ventricle LV may be referred to as epicardial anchors.

Figure 5A:
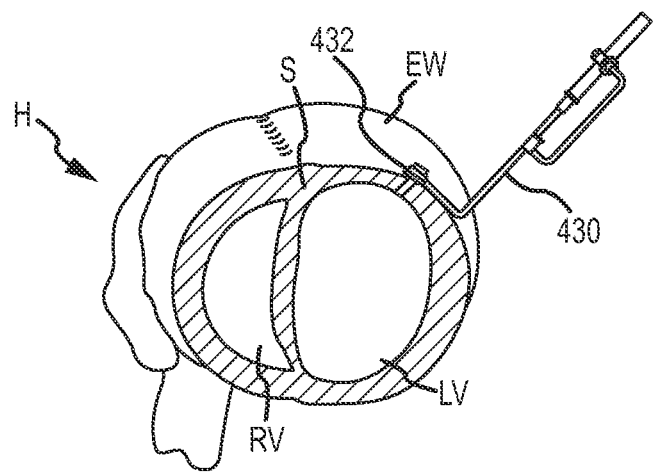
FIG. 5A illustrates a tissue anchoring device positioned adjacent an external wall of a heart in a treatment for congestive heart failure.

As can be understood with reference to FIG. 5A, a selected location for perforation of the external wall EW can be identified using an image from a thoracoscope/fluoroscope, optionally in combination with an image from another imaging modality (such as a prior or contemporaneous image from an ultrasound imaging system, an MRI imaging system, an X-ray or fluoroscopic imaging system, a CT imaging system, or the like). The heart tissue gripping device 430 may then be advanced through an incision in the body (e.g., subxiphoid incision) to position the tissue gripping member 432 adjacent the selected location for perforation. The heart tissue gripping device 430 may be advanced through the body and the tissue gripping member 432 positioned at the selection location while heart is beating.

Tissue gripping device 430 may be positioned adjacent the external wall EW by inserting the tissue gripping member 432 through a subxiphoid incision and positioning the tissue gripping member 432 adjacent the external wall EW. The subxiphoid incision may be relatively small, such as a two or three finger incision. A vacuum may then be applied to attach the tissue gripping member 432 to the external wall EW (e.g., epicardial tissue, pericardial tissue, and the like).

Figure 5B:
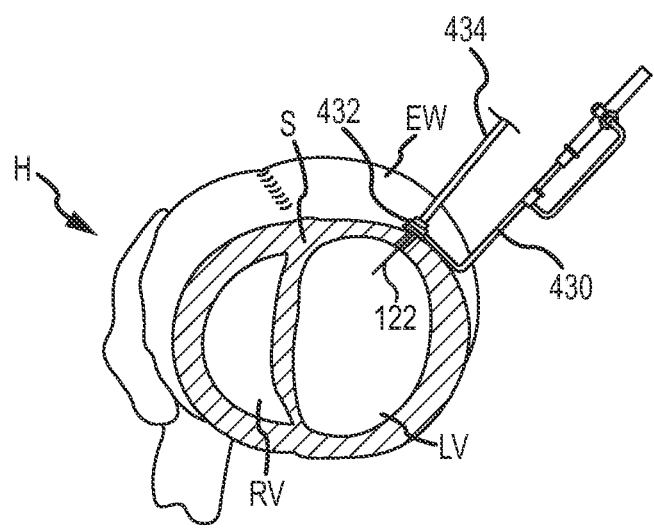
FIG. 5B illustrates a tissue penetrating device coupled with the tissue anchoring device and a needle of the tissue penetrating device penetrating through the external wall of the heart in the congestive heart failure treatment.

As shown in FIG. 5B, with the tissue gripping member 432 positioned adjacent external wall EW, a tissue penetrating device 434 may then be inserted into the body and coupled with the tissue gripping member 432. The tissue penetrating device 434 may be inserted between an incision between ribs of the patient, such as between the fourth and fifth intercostal space, and/or through a cannular member as described above. The cannular member may axially align, or otherwise align, the tissue penetrating device 434 with the tissue gripping member 432. The tissue penetrating device 434 may be actuated to advance a needle 122 beyond the tissue gripping member 432 to penetrate the external wall EW (e.g,. epicardial tissue, pericardial tissue, and the like). In some embodiments, a pressure sensing element of the needle 122, or other device, may be used to determine that the needle 122 is positioned adjacent the external wall EW and/or inserted through the external wall EW and into the left ventricle LV.

A guidewire (not shown) may then be inserted through the external wall EW and through a septal wall S to allow a tether or tension member and one or more anchors to be positioned adjacent and engage the septal wall S. For example, a catheter (not shown) may be inserted into the arterial vasculature via the jugular artery JA and tricuspid valve; or in other embodiments, via the femoral artery FA and inferior vena cava IVC, via the via the superior vena cava, or the like. A snare device (not shown), such as a wire hoop or wire basket, may then be positioned against the septum S at or adjacent an insertion point for the needle 122. The snare device may provide a target for the needle 122 and the needle may be used to penetrate the septal wall S. The guidewire may then be inserted through the external wall EW and septal wall S and captured by the snare device. An additional description of this procedure is provided in the '849 application, which is incorporated by reference herein.

Figure 5C:
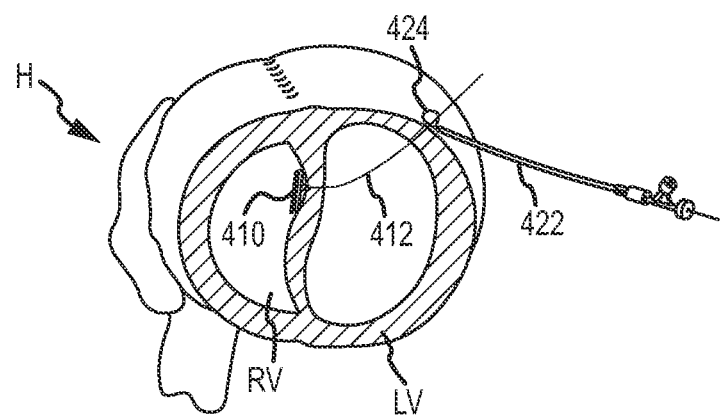
FIG. 5C illustrates a septal anchor positioned adjacent the septal wall and a fastening member fastened with a tension member that extends through the septal wall and external wall in the congestive heart failure treatment.

As shown in FIG. 5C, a tether or tension member 412 is then inserted through the external wall EW and through a septal wall S. A septal anchor 410, that is coupled with a distal end of the tension member 410, is positioned adjacent septum S within right ventricle RV. Tension member 412 extends from septal anchor 410, through septum S and into left ventricle LV, through external wall EW, and through a lumen of the tissue gripping device 430. At this point, the tissue gripping device 430 may be detached from the external wall EW (via removal of the vacuum and the like) and removed from the body. Subsequent to or during removal of the tissue gripping device 430, a fastening component 422 may be employed to fasten with or grip the tension member 412. To grip the tension member 412, a wire noose 424 may be removed from an annular groove of the tissue gripping member 432. The wire noose 424 may then be moved axially downward relative to the tissue gripping member 432 and over and around the tension member 412. The wire noose 424 may already be positioned around tension member 412 due to the wire noose 424 being "preloaded" or coupled with the tissue gripping member and the tension member 412 being disposed within the lumen of tissue gripping member 432. The wire noose 424 may then be cinched around the tension member 412 to fasten with or grip the tension member 412. With the wire noose 424 cinched around the tension member 412, the fastening component 422 may be pressed against the external wall EW to provide hemostasis or additional hemostasis to the external wall perforation.

The tissue gripping member 432 may then be removed from the body via the subxiphoid incision. Removing the tissue gripping device 430 may cause the tension member 412 to be pulled through the subxiphoid incision since the tension member 412 is disposed through a lumen of the bell-shaped tissue gripping member 432. In other embodiments, the tissue gripping member 432 may have an opening, channel, or U-shape that allows the tissue gripping member 432 to be pulled off and/or around the tension member 412 without puling the tension member 412 through the subxiphoid incision.

Figure 5D:
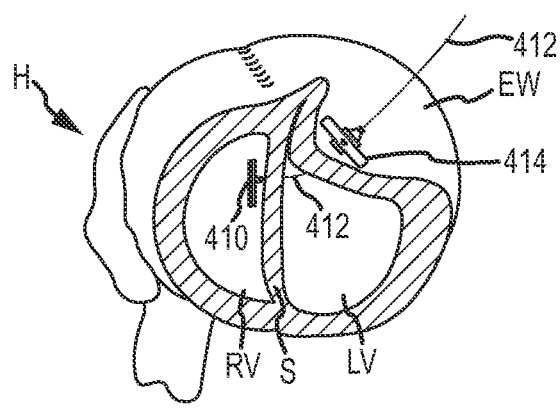
FIG. 5D illustrates an epicardial anchor being slid distally along the tension member and adjacent the external wall of the heart in the congestive heart failure treatment.

As shown in FIG. 5D, an epicardial anchor 414 is then coupled with tension member 412 and slid distally along tension member 412 until the epicardial anchor 414 is positioned adjacent external wall EW. The epicardial anchor 414 may be inserted within the subxiphoid incision since the tension member 412 is pulled through the subxiphoid incision by the tissue gripping member 432. The epicardial anchor 414 may be relatively large and access through the subxiphoid incision may make positioning the epicardial anchor 414 adjacent the external wall EW significantly less difficult in comparison to accessing the external wall EW through a typically small incision between the ribs. In other embodiments, however, an oval access port may be used between ribs to allow the epicardial anchor to be inserted between the ribs with minimal effort.

An epicardial anchor application device (not shown) may be used to slide epicardial anchor 414 distally along the tension member 412 to the external wall EW. The epicardial anchor application device may also be used to apply tension between septal anchor 410 and epicardial anchor 414 to urge or bring the septum S and external wall EW together. Exemplary embodiments of epicardial anchor application devices that may be used to slide and/or tension the anchors are described in U.S. Provisional application Ser. No. 61/872,568, filed Aug. 30, 2013 and entitled "Heart Anchor Positioning Devices, Methods, and Systems for Treatment of Congestive Heart Failure and Other Conditions," the entire disclosure of which is incorporated by reference herein.

Prior to tensioning the septal and epicardial anchors, 410 and 414, the tension member 412 may be rerouted from the subxiphoid incision to an incision between the ribs that is positioned above the external wall perforation. This may allow the epicardial anchor application device to have a direct line access to the epicardial anchor 414. The epicardial anchor 414 may then be locked in place about tension member 412 to prevent the epicardial anchor 414 from moving about tension member 412 and to keep the septum S and external wall EW in position relative to one another. Exemplary embodiments of epicardial anchors 414 and epicardial anchor application devices 422 and uses therefore are described in U.S. patent application Ser. No. 13/632,104, filed Sep. 30, 2012 and entitled "Trans-catheter Ventricular Reconstruction Structures, Methods, and Systems for Treatment of Congestive Heart Failure and other Conditions," the entire disclosure of which is incorporated herein by reference.

Figure 5E:
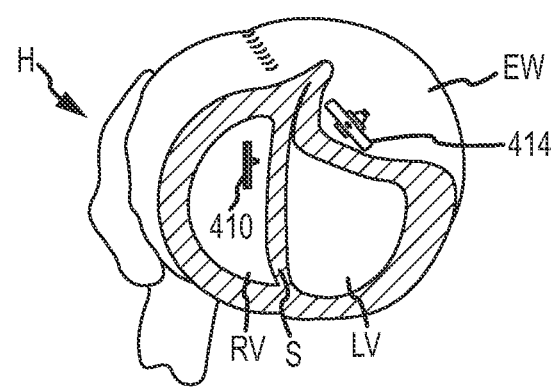
FIG. 5E illustrates the septal anchor and epicardial anchor being used to reconfigure the shape of the heart and the volume of the left ventricle in the congestive heart failure treatment.

As shown in FIG. 5E, after the septal anchor 410 and epicardial anchor 414 are tensioned so that the septum S and external wall EW are brought together, the tension member 412 proximal to epicardial anchor 414 may be cut and discarded. The septal anchor 410 and epicardial anchor 414 may be left in position relative to septum S and external wall EW with the heart H reconfigured to reduce a volume of left ventricle LV and exclude scar tissue from the left ventricle LV. The above process may be repeated a plurality of times to position additional septal anchors 410 and/or epicardial anchors 414 about the septum S and external wall EW. The anchors may be aligned about a desired contour of the heart, such as a contour defined by scar tissue and the like. In some embodiments, the contour for placement of multiple anchors may be determined via an image of the heart and insertion points for the anchors may be calculated or measured from the image. The insertion points may then be mapped or marked on the heart, such as by using a template or pattern. In this manner, the shape of heart H and the volume of left ventricle LV may be reconfigured as desired.

Figure 6:
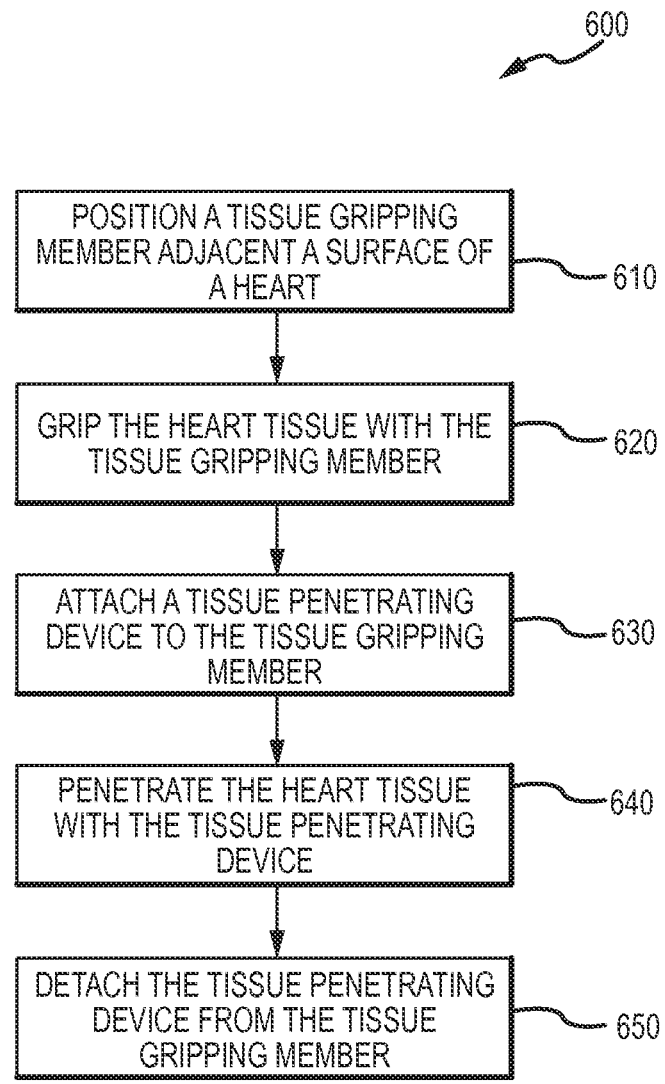
FIG. 6 illustrates a method for penetrating tissue of a heart wall, according to an embodiment.

FIG. 6 illustrates a method for penetrating tissue of a heart wall. At block 610, a tissue gripping member of a heart tissue gripping device is positioned adjacent a surface of the heart. At block 620, tissue of the heart surface is gripped with the tissue gripping member so as to releasably attach the tissue gripping member to the heart surface. At block 630, a tissue penetrating device is attached to a coupling of the tissue gripping member. At block 640, the tissue of the heart wall is penetrated with the tissue penetrating device and at block 650, the tissue penetrating device is detached from the coupling of the tissue gripping member.

In some embodiments, attaching the tissue penetrating device to the coupling of the tissue gripping member is achieved by inserting a distal tip of the tissue penetrating device into a threaded aperture of the tissue gripping device. In another embodiment, attaching the tissue penetrating device to the coupling of the tissue gripping member is achieved by inserting a distal tip of the tissue penetrating device into a ball and socket joint of the tissue gripping device.

In some embodiments, the tissue gripping member is coupled with a distal end of an elongate shaft. In such embodiments, the method may also include bending or adjusting the elongate shaft to allow the tissue gripping member to be inserted through an incision and positioned adjacent the heart surface at a position that is substantially offset from an axis of the elongate shaft. The elongate shaft may be sufficiently rigid so as to resist bending as the tissue gripping member is inserted and positioned within the body.

In some embodiments, the method may further include inserting a tension member through the heart wall penetration and into a chamber of the heart, gripping the tension member with a fastening component of the heart tissue gripping device, and removing the tissue gripping member from the body. The fastening component may provide hemostasis to the heart wall by gripping the tension member. In some embodiments, gripping the tension member may be achieved by tensioning a wire noose to cinch the wire noose around the tension member. Prior to cinching the wire noose around the tension member, the wire noose may be uncoupled from an annular channel of the tissue gripping member.

Figure 7:
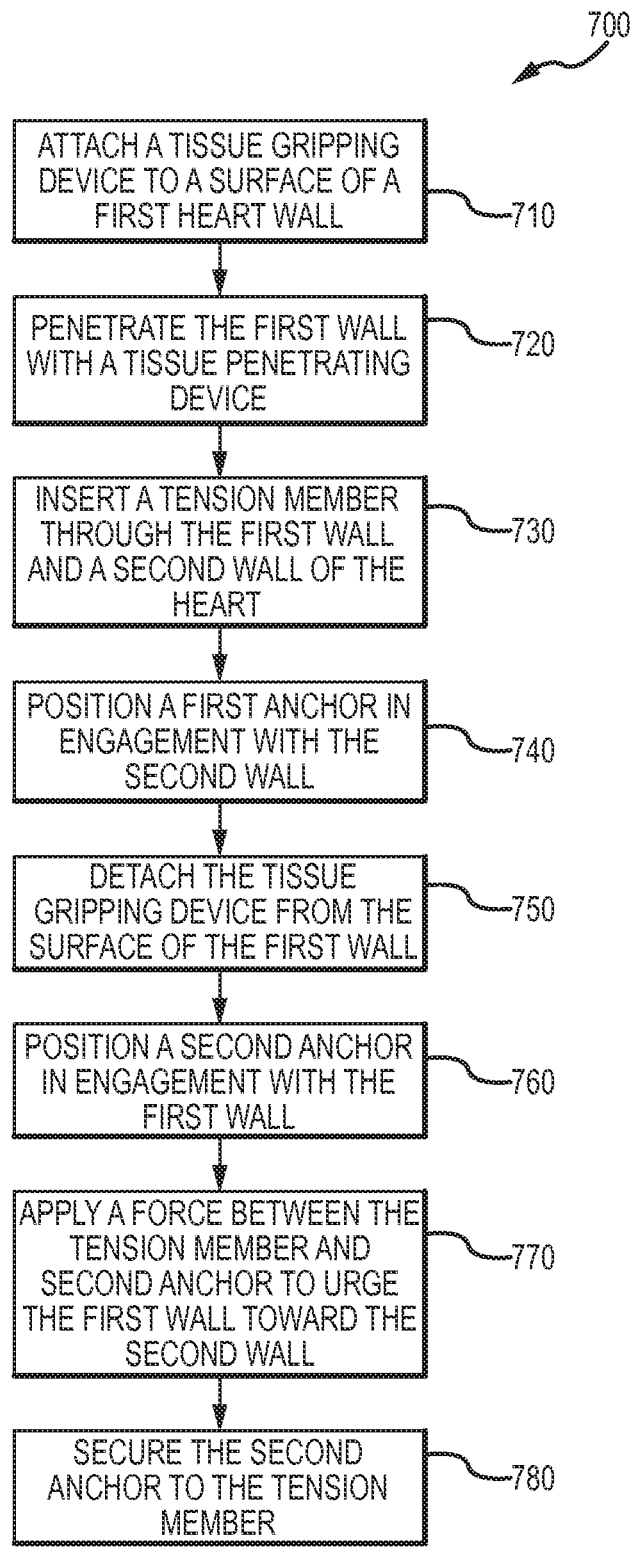
FIG. 7 illustrates a method for treating a heart, such as for treatment of congestive heart failure, according to an embodiment.

FIG. 7 illustrates a method for treating a heart. At block 710, a device is attached to a surface of a first wall of the heart by gripping the heart tissue with a tissue gripping member of the device. At block 720, the tissue of the first wall of the heart is penetrated with a tissue penetrating device. At block 730, a tension member is inserted through the first wall of the heart and through a second wall of the heart. A chamber (i.e., left ventricle) separates the first wall and second wall. At block 740, a first anchor is positioned in engagement with the second wall. The first anchor is coupled with or otherwise attached to the tension member. At block 750, the device is detached from the surface of the first wall of the heart by releasing the heart tissue with the tissue gripping member. At block 760, a second anchor is positioned in engagement with the first wall of the heart. The second anchor is slidably coupled with the tension member to allow the second anchor to slide proximally and distally along a length of the tension member. At block 770, an anchor force is applied between the tension member and the second anchor so that the first anchor urges the second wall toward the first wall and the second anchor urges the first wall toward the second wall. At block 780, the second anchor is secured to the tension member to restrict proximal movement of the second anchor along the tension member. In some embodiments, the first wall and the second wall are brought into engagement by applying the anchor force between the tension member and the second anchor.

In some embodiments, the tissue penetrating device may be attached to a coupling of the tissue gripping member prior to penetrating the tissue of the first wall. In such embodiments, the tissue penetrating device may be detached from the coupling after penetrating the tissue of the first wall. In some embodiments, the tension member may be gripped with a fastening component of the device to provide hemostasis to the first wall as the device is detached and removed from the surface of the first wall. In such embodiments, the fastening component may be a wire noose. The wire noose may be uncoupled from an annular channel of the tissue gripping member and cinched around the tension member to grip the tension member and provide hemostasis to the first wall.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A heart tissue gripping device comprising:
   a body portion that is grippable by a user to allow the user to control the device such that one or more components of the device are insertable through an incision in a body to position the one or more components adjacent a surface of the heart;
   an elongate shaft having a proximal end coupled with the body portion and a distal end;
   a tissue gripping member that is fixedly coupled to the distal end of the elongate shaft so that the tissue gripping member is fixed in position relative to the distal end of the elongate shaft, the tissue gripping member having a main body and a lumen extending coaxially through the main body from a proximal most end of the main body to a distal most end of the main body, the tissue gripping member being insertable through the incision in the body so that the entire tissue gripping member is positionable within the body and against the heart surface when the tissue gripping member is inserted through the incision, the tissue gripping member being configured to releasably attach to tissue of the heart surface, wherein the distal end of the elongate shaft is attached to and extends laterally from a sidewall of the main body between the distal most end and the proximal most end of the main body such that the elongate shaft extends off-axis from the lumen of the tissue gripping member and such that when the tissue gripping member is inserted within the incision, the proximal most end of the main body is disposed within the body so as to be exposed to the surrounding environment within the body while the distal most end of the main body is positioned against the heart surface; and
   a coupling feature for releasably attaching a catheter device and/or tissue penetrating device to the tissue gripping member to allow said device to access the tissue of the heart surface;
   wherein the proximal end of the elongate shaft is directly coupled to the body portion such that when the entire tissue gripping member is positioned within the body and against the heart surface, at least a portion of the elongate shaft is configured to remain outside the incision in the body.

2. The device of claim 1, wherein the elongate shaft is directly coupled to the body portion so that as the user manipulates the body portion outside the incision in the body, the elongate shaft maneuvers the tissue gripping member and controls the motion and movement of the tissue gripping member, and wherein the elongate shaft is malleable such that the tissue gripping member is insertable through the incision and positionable adjacent the heart surface with the tissue gripping member substantially offset from an axis of the elongate shaft, and wherein the elongate shaft is sufficiently rigid so as to resist bending as the tissue gripping member is inserted and positioned maneuvered within the body.

3. The device of claim 1, further comprising a fastening component that is configured to releasably fasten with a tension member that is inserted through a wall of the heart to allow the tissue gripping member to be removed from the body while providing hemostasis to the heart wall.

4. The device of claim 3, wherein the fastening component is a wire noose that is cinchable around the tension member by tensioning the wire noose.

5. The device of claim 4, wherein the tissue gripping member comprises an annular channel formed on an exterior surface that is configured to receive the wire noose to allow the wire noose to be releasably coupled with the tissue gripping member.

6. The device of claim 1, further comprising a second shaft having a proximal end coupled with the body portion and a distal end coupled with a cannular member, the cannular member having a lumen through which one or more devices are insertable, the second shaft being malleable to allow the cannular member to be coaxially aligned with and positioned above the tissue gripping member while the tissue gripping member is attached to the heart surface and while the cannular member is positioned outside the body.

7. The device of claim 1, wherein the tissue gripping member is switchable between an on-state in which the tissue gripping member attaches with the heart tissue and an off-state in which the gripping member detaches from the heart tissue.

8. The device of claim 1, wherein the coupling feature comprises a threaded central lumen of the tissue gripping member.

* * * * *